United States Patent [19]

Curtiss

[11] Patent Number: 5,694,206
[45] Date of Patent: Dec. 2, 1997

[54] SPECTROPHOTOMETRIC SYSTEM USING A PH/ISE METER FOR CALIBRATION

[75] Inventor: Brian Curtiss, Boulder, Colo.

[73] Assignee: Analytical Spectral Devices, Inc., Boulder, Colo.

[21] Appl. No.: 608,619

[22] Filed: Mar. 1, 1996

[51] Int. Cl.[6] ............................. G01J 3/51; G01N 21/64
[52] U.S. Cl. .......................... 356/72; 356/414; 356/417
[58] Field of Search ............................. 356/72, 417, 414

[56] References Cited

U.S. PATENT DOCUMENTS

| | | |
|---|---|---|
| 3,164,663 | 1/1965 | Gale . |
| 3,441,352 | 4/1969 | Hughes . |
| 3,740,155 | 6/1973 | Keller et al. ............... 356/246 |
| 4,152,075 | 5/1979 | Rellstab et al. ............ 356/435 |
| 4,912,417 | 3/1990 | Gibboney et al. .......... 324/438 |
| 5,077,481 | 12/1991 | Hoult ......................... 250/576 |
| 5,124,659 | 6/1992 | Frola et al. ................. 324/438 |
| 5,570,176 | 10/1996 | Noel .......................... 356/73.1 |

*Primary Examiner*—Vincent P. McGraw
*Attorney, Agent, or Firm*—Dorr, Carson, Sloan & Birney, P.C.

[57] ABSTRACT

A spectrophotometric system uses an immersible spectrophotometric probe that can be directly interfaced to a pH/ISE meter for calibration and read-out. The probe contains a light source, a photodetector, and interface circuitry for converting the signal from the photodetector to an output voltage within a predetermined range suitable for the pH/ISE meter (e.g., 0-1.8 volts). The probe housing can also include a sample chamber to provide a predefined optical path from the light source through a portion of the sample fluid to the photodetector. An optical filter can be included in the optical path to allow measurements within a selected wavelength range. The pH/ISE meter receives the output voltage from the probe, applies a calibration function, and displays the resulting value. In the preferred embodiment, the probe is designed as a unitary structure that is plug-compatible with most conventional pH/ISE meters. This allows the present spectrophotometric probe to be used interchangeably with conventional pH probes and other ISE probes.

20 Claims, 4 Drawing Sheets

SPECTROPHOTOMETRIC SYSTEM USING A PH/ISE METER FOR CALIBRATION

BACKGROUND OF THE INVENTION

1. Field of the Invention

The present invention relates generally to the field of spectrophotometers. More specifically, the present invention discloses a spectrophotometric probe that can be interfaced to a pH/ISE meter for calibration and read-out.

2. Background of the Invention

Currently, no device exists that allows use of a pH/ISE meter for performing spectrophotometric measurements. Instead, a separate spectrophotometric instrument must be purchased for this purpose.

Electrochemical probes responsive to a wide variety of ionic species are well known. These probes produce a voltage potential that is proportional to the negative log of the activity of a specific ion. This value is typically referred to as pX, where X is the chemical symbol of the ion being sensed. The most common of these, the pH electrode, measures the activity of the hydronium cation. In recent years, several new classes of ion selective electrodes (ISE) have been introduced for a wide variety of ion species. Through appropriate calibration methods, a direct relationship between ion concentration and the ISE potential can be formulated for each ion species.

The pH electrode or ISE is typically connected to a pH meter. This device is a very high impedance electronic voltmeter that draws negligible current from the electrode. The meter applies a conversion function to the voltage supplied by the electrode and displays the resulting pX value (or pH for hydronium cations). Many meters are now microprocessor controlled, allowing the application of an appropriate calibration function to generate and display concentration values (e.g., in units such as ppm).

The conversion function between the ISE probe voltage and pX (or concentration) must be calibrated for each probe. Several analytical techniques are available for the conversion of the electrode potential into concentration units. Two of the most common are direct multi-point calibration and known addition. In the direct calibration procedure, electrode potentials of standard solutions with known concentrations are measured. A calibration equation is then determined using these known data points that relates the electrode potential to the ion concentration. Except for low concentration levels, this is typically a linear negative log relationship, as shown in FIG. 4. In the log-linear response region, only two standards are needed to specify a calibration equation (i.e., by calculating the slope and offset of the line). In non-log-linear regions, more standards must be measured to adequately define the calibration function. The concentration of an unknown solution can then be determined by applying the calibration function to the measured potential of the electrode when immersed in the unknown solution.

For pH probes, the probe is inserted into several pH buffers (having a known pH) and readings are stored. The software in the pH meter then computes a slope and offset. These values can then be applied to the measured probe output voltage for an unknown sample to make the conversion to pH. In older analog pH meters, adjustment dials were provided to manually adjust the pH scale.

A similar technique is used for ISE probes. The output of the probe when placed in several solutions of known concentration is recorded and used to perform the calibration. The concentration (rather than pH) is usually the value for which meter is calibrated. With older analog meters, the user records the millivolt readings for the calibration solutions and then performs the calibration manually. The calibration curve can then be used to "look up" the concentration value corresponding to the ISE's millivolt reading when inserted in a sample.

The method of known addition does not require the measurement of standard samples. The electrode potential, in millivolts, of the unknown solution is measured before and after the addition of a known volume of a standard solution with a known concentration of the ion to be measured. The concentration of the ion in the unknown solution is then computed using the following equation:

$$C_{sample} = QC_{standard}$$

where:

$C_{sample}$ is the sample concentration $C_{standard}$ is the concentration in the standard solution $$Q = \frac{p}{(1+p)*10^{\Delta E/S} - 1}$$

p is the ratio of the volume of the standard to that of the sample.

S is the change in the electrode potential for a tenfold concentration change (in millivolts).

ΔE is the difference in electrode potential between the two meter readings.

Spectrophotometers

The prior art includes probe colorimeters that incorporate the light source and all of the calibration electronics (including read-out) into a single hand-held probe. However, the spectrophotometers that have become widely used include a probe that is immersed or dipped into the sample liquid and a separate instrument that includes a light source to deliver light to the probe through an optical fiber. After passing through the sample liquid, the light is collected by another optical fiber and delivered back to the instrument where the intensity of the collected light is measured by a photodetector. Many units permit the light to be filtered either at the light source before it is sent to the probe, or at the photodetector after it has been delivered back to the instrument. The instrumentation unit applies a calibration function to the output voltage from the photodetector and displays the resulting value. Different types of probes and instrumentation units can be used to measure total transmissivity by the sample or transmissivity within selected frequency bands (i.e., colorimetric analysis), or to measure the intensity of light emitted by the sample resulting from fluorescence or Raman scattering.

Colorimetry is one of the most widely used forms of spectrophotometric analysis. In this technique, light is passed through a sample and the percentage of light absorbed at a particular wavelength is measured. The chosen wavelength is generally one at which the ion of interest has significant absorbance. Since the amount of light absorbed depends on the concentration of the absorbing substance in the sample, it is possible to quantitatively determine the amount present. When light passes through an absorbing substance, the incident intensity ($I_o$) will be greater than the intensity of the transmitted beam (I). Transmittance is defined as the ratio of the incident to transmitted energy:

$$T = \frac{I}{I_o}$$

Concentration of ions in solution can be calculated from the measured transmissivity of the solution using Beer's law:

$$-\log(T) = \epsilon bc$$

where:

$\epsilon$ is the molar absorptivity constant for the ion being measured b is the path length of light through the sample c is the concentration of the ion being measured in the solution Thus, both the potentiometric and spectrophotometric methods rely on a similar log-linear relationship between the measured parameter and ion concentration. The methods outlined above for potentiometric analysis are identical to those used in spectrophotometric analysis (i.e., standard addition, standard subtraction, and simple multipoint calibration). In the case of potentiometry, the quantity measured is the output potential of the electrochemical probe (e.g., the pH electrode or other ISE probes). For spectrophotometry, the measured parameter is the output voltage of the photodetector. The primary difference is that the ISE method uses a log relationship, while the spectrophotometric method uses a power of 10 relationship. In spectrophotometric analysis, the transmission signal is converted to absorbance by taking the negative log of the transmission. Thus, the absorbance value is proportional to the ion concentration. In the ISE method, the signal is proportional to the log of the concentration.

Prior Art

A wide variety of spectrophotometric probes and related equipment have used in the past, including the following:

| Inventor | Patent No. | Issue Date |
|---|---|---|
| Gale | 3,164,663 | Jan. 5, 1965 |
| Hughes | 3,441,352 | Apr. 29, 1969 |
| Keller et al. | 3,740,155 | June 19, 1973 |
| Rellstab et al. | 4,152,075 | May 1, 1979 |
| Gibboney et al. | 4,912,417 | Mar. 27, 1990 |
| Hoult | 5,077,481 | Dec. 31, 1991 |
| Frola et al. | 5,124,659 | June 23, 1992 |

Hughes discloses a colorimeter using interchangeable meters. Each meter is relevant to one particular test and is calibrated for direct reading in conjunction with a selected one of a plurality of photoelectric cells. Switches are employed to insert and remove each meter into an electric circuit with the appropriate cell.

Gale discloses an example of a colorimetric probe having a light source 21, a photodetector 23, and a sample chamber at the lower end of the probe.

Keller et al., Rellstab et al., and Hoult disclose other examples of immersible optical probes having sample chambers.

Frola et al. and Gibboney et al. disclose examples of microprocessor-controlled pH and ion concentration meters.

None of the prior art references uncovered in the search show a spectrophotometric system that interfaces a spectrophotometric probe with a pH/ISE meter. The present system enables existing owners of pH/ISE meters to readily perform spectrophotometric analyses. The spectrophotometric probe in the present system is designed to be plug-compatible with most conventional pH/ISE meters. This allows laboratory personnel to quickly and easily switch between spectrophotometric analysis and potentiometric analysis simply by substituting probes connected to a pH/ISE meter.

This significantly also reduces the cost of the system in comparison to conventional spectrophotometric units used for calibration and read-out. For example, a pH/ISE meter can be purchased for as little as a few hundred dollars. In contrast, many spectrophotometers cost several thousand dollars.

SUMMARY OF THE INVENTION

This invention provides a spectrophotometric probe that can be directly interfaced to a pH/ISE meter for calibration and read-out. The probe contains a light source, a photodetector, and interface circuitry for converting the signal from the photodetector to an output voltage within a predetermined range suitable for the pH/ISE meter (e.g., 0–1.8 volts). The probe housing includes a sample chamber to provide a predefined optical path from the light source through a portion of the sample fluid to the photodetector. An optical filter can be included in the optical path to allow measurements within a selected wavelength range. The pH/ISE meter receives the output voltage from the probe, applies a calibration function, and displays the resulting value. In the preferred embodiment, the probe is designed as a unitary structure that is plug-compatible with most conventional pH/ISE meters.

A primary object of the present invention is to provide a spectrophotometric probe that can be directly interfaced to a conventional pH/ISE meter.

Another object of the present invention is to provide a low cost system for spectrophotometric analysis by eliminating the need for conventional spectrophotometric units.

Yet another object of the present invention is to provide a spectrophotometric probe that can be used interchangeably with pH or ISE probes. This enables a conventional pH/ISE meter to be used both for potentiometric analysis and for spectrophotometric analysis simply by switching probes.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

The present invention is based on recognition that the methods used for calibration of pH/ISE meters, including direct multi-point calibration and known addition, are equally applicable to spectrophotometric methods. Potentiometric and spectrophotometric determinations of the concentrations of ions in solution both rely on the same log-linear relationship between the measured parameter and ion concentration. In the case of potentiometry, the quantity measured is the output potential of the electrochemical probe (e.g., the pH electrode or other ISE probes). For spectrophotometry, the measured parameter is the output voltage of the photodetector. Because these parameters are both voltages, the calibration circuitry designed for potentiometry (i.e., the pH/ISE meter) will also serve for spectrophotometric measurements.

A primary requirement is to match the electrical output characteristics of the spectrophotometric probe to the input specifications of the pH/ISE meter. Meters that are intended only for pH measurements typically have an input range of ±800 millivolts. Meters that are intended for use with ISE probes (in addition to pH electrodes) typically have an input range of ±1800 millivolts. The very small current produced by an electrochemical probe dictates that pH/ISE meters must have a very high input impedance. Thus, the spectrophotometric probe should generate an analog signal having a voltage range matching that of a pH/ISE meter.

It is also important that the spectrophotometric probe match at least some of the physical dimensions of conventional pH/ISE probes. The outside diameter of the probe 20 housing should be approximately 12 mm to match that of a pH/ISE probe. In addition, the lower portion of the cap 22 should match that of a pH/ISE probe (i.e., 16 mm) to fit into existing probe holders.

Figure 1:
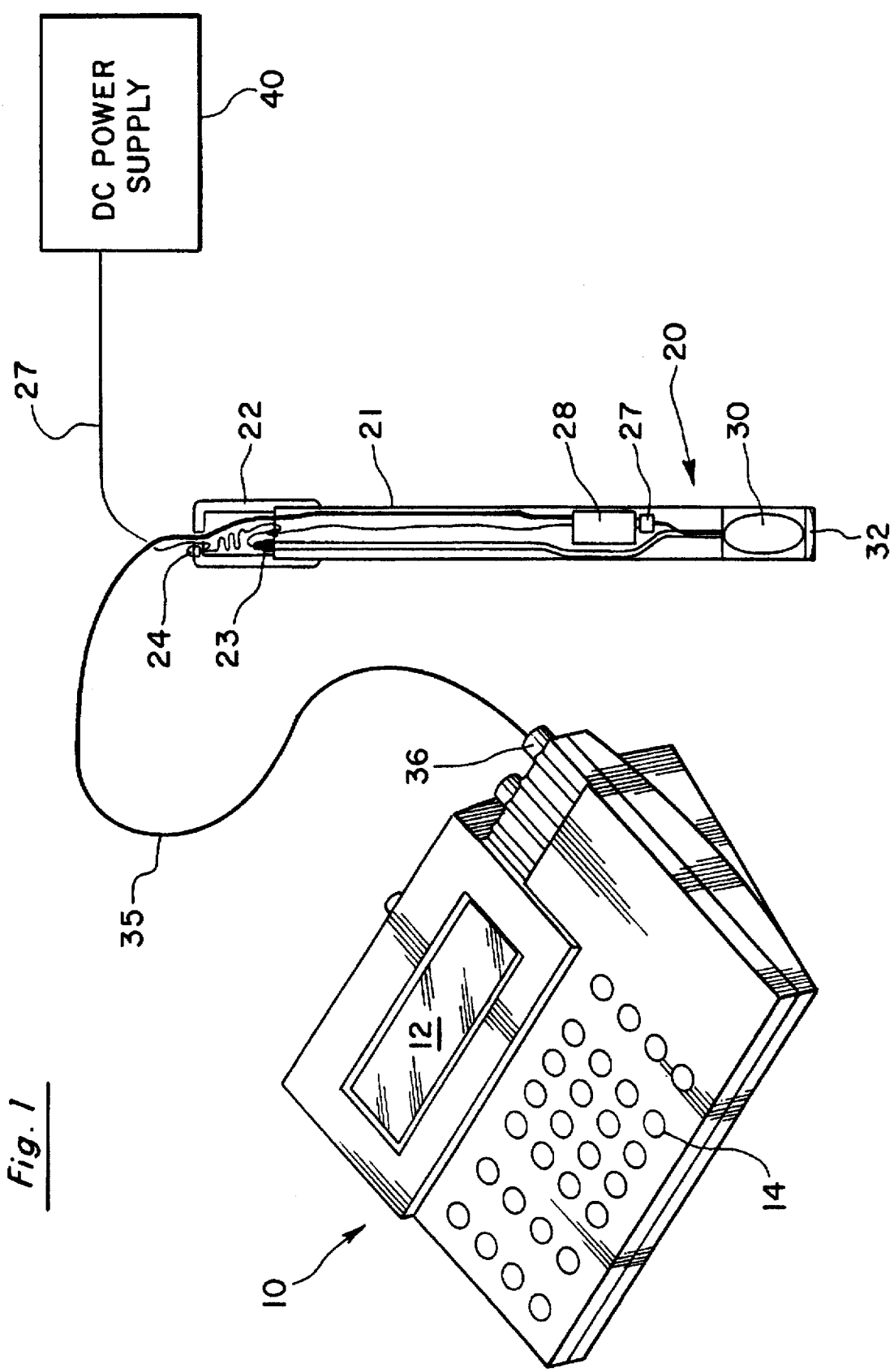
FIG. 1 is a schematic diagram showing the spectrophotometric probe interfaced to a pH meter.
Figure 2:
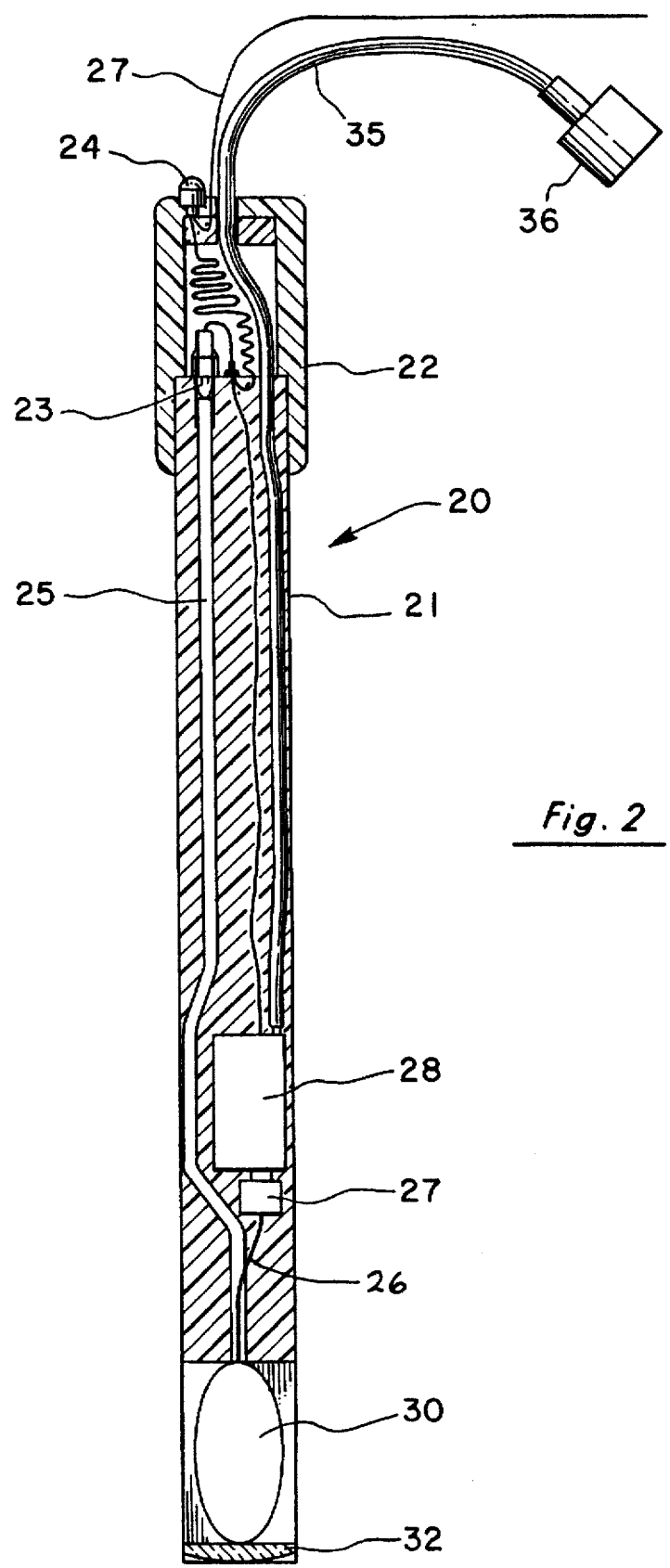
FIG. 2 is a schematic cross-sectional view of the spectrophotometric probe 20.

Turning to FIG. 1, a schematic diagram is provided of the entire system, including the probe assembly 20, pH/ISE meter 10, and power supply 40. FIG. 2 shows a more detailed cross-sectional view of the probe assembly 20. The probe 20 has a unitary housing 21 made of glass, polymer, or stainless steel. An cap 22 is held by friction fit on the upper end of the housing 21. In the preferred embodiment, the housing 21 has a diameter of approximately 12 mm and a length of approximately 130 mm. The cap 22 has a diameter of approximately 16 mm and a length of approximately 30 mm. The components within the housing 21 can be potted in epoxy resin to make the probe assembly 20 more rugged. At minimum, at least the bottom portion of the probe assembly should be suitable for immersion in the sample fluid. The only external leads are the output voltage lead 35 connected to the pH/ISE meter and the power cord 27 leading to the DC power supply 40, as shown in FIG. 1

The components within the probe assembly 20 include an on/off switch 24 with an LED "power on" indicator. A low voltage DC light bulb 23 serves as the light source. An illumination optical fiber 25 carries light from the light source 23 to the sample chamber 30 at the bottom of the probe. The sample chamber 30 is open to the sample fluid in the surrounding container. A series of holes are placed in sample chamber 30 to allow fluids to easily enter into the probe 20. The holes extend to the top of the sample cavity 30 to prevent the entrapment of bubbles. A reflector 32 located at the bottom of the sample cavity 30 reflects and focuses light on the return optical fiber 26 leading from the sample chamber 30 to a photodetector 27. For example, a plano-convex lens with a mirrored bottom surface can be used as the reflector 32, although a convex stainless steel reflector is substantially less expensive.

The photodetector assembly 27 generates an output voltage proportional to the intensity of light received within a desired frequency band, which can then be used as an indication of the transmissivity of the sample fluid. The photodetector assembly 27 typically includes an optical bandpass filter mounted over a photodetector. The filter is selected to allow transmission in the wavelength band of interest while excluding light outside of this wavelength range. Thus, the sample chamber is designed to provide a well-defined optical path from the end of the illuminating optical fiber 25 through a portion of said sample fluid and back to the return fiber optics 26 leading to the photodetector assembly 27.

A bandpass filter can be placed in the photodetector window to limit the spectrophotometric analysis to a desired wavelength, or the return optical fiber 26 can be mated directly to the photodetector window without the benefit of a filter. The probe can also be equipped with interchangeable filters to facilitate switching between wavelengths of interest.

Interface circuitry 28 converts the output voltage from the photodetector 27 into a range compatible with the input voltage range for a conventional pH/ISE meter (i.e., approximately zero to 1.8 volts). An op-amp operating as a linear amplifier with a fixed gain is employed for this purpose in the preferred embodiment. The output voltage of the interface circuitry 28 is fed through a coaxial cable 35 to a standard BNC connector 36 that can be plugged into the input jack of a pH/ISE meter 10, as illustrated in FIG. 1.

Figure 3:
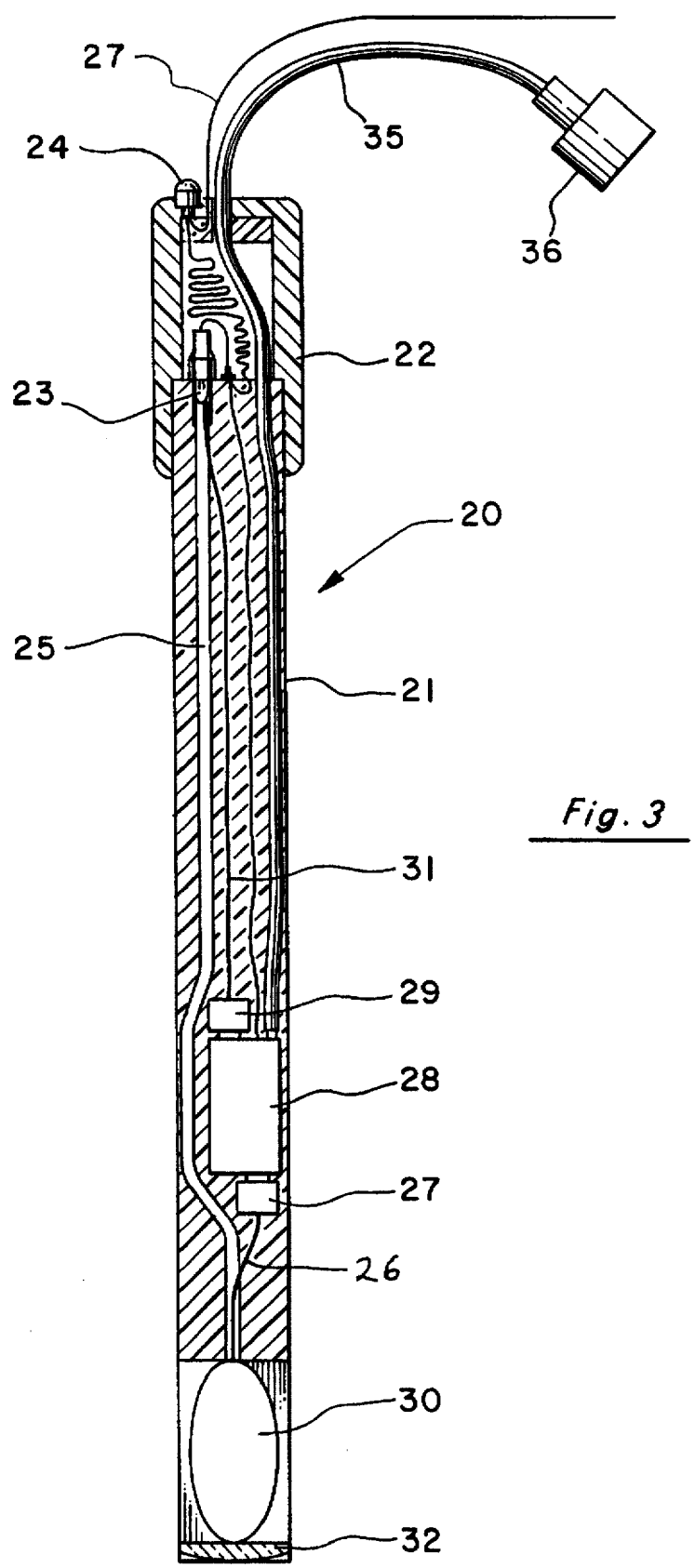
FIG. 3 is a schematic cross-sectional view of an alternative embodiment of the spectrophotometric probe 20 incorporating dual photodetectors 27 and 29.

FIG. 3 shows an alternative embodiment of the probe assembly 20 with dual photodetectors 27 and 29. The second photodetector 29 directly monitors the intensity of the light source 23 through a third optical fiber 31 and generates a reference voltage that is used by the interface circuitry 28 to normalize the output voltage of the first photodetector 27 to compensate for variations in the intensity of the light source. For example, the interface circuitry 28 can be configured to output a voltage proportional to the ratio of the sample and reference detector voltages. The embodiment is intended primarily for applications requiring a high degree of high photometric stability.

Figure 4:
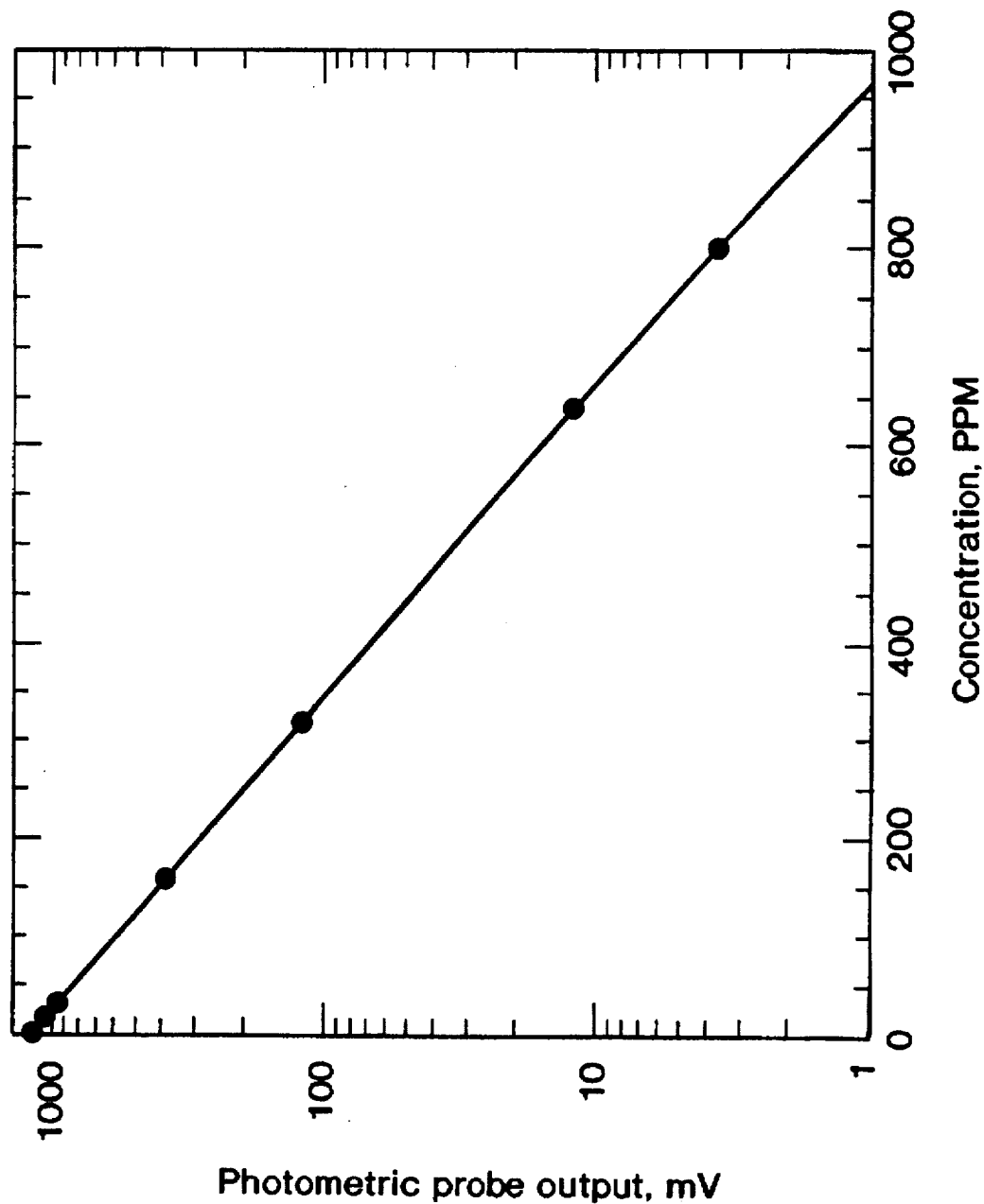
FIG. 4 is a chart showing the linear negative log relationship typically used in the calibration function by a pH/ISE meter.

The pH/ISE meter 10 contains a microprocessor that can be programmed with an arbitrary calibration function to convert input voltages from the probe 20 into an output value displayed on an analog or digital display 12. The output value can be expressed in terms of concentration (percentage or ppm), percentage absorption, etc., as required by the user. The calibration function is typically a linear negative log relationship as discussed above and shown in FIG. 4. The pH/ISE meter usually also includes a keypad 14 that allows the user to control operation of the meter and enter data. Thus, the probe 20 is designed as a unitary structure that is plug-compatible with most conventional pH meters and ISE meters capable of providing the required calibration and display functions.

The spectrophotometric probe 20 can be used interchangeably with conventional pH probes and other ion-selective electrodes to provide a number of types of colorimetric analyses. For example, the probe 20 can be used as a turbidity sensor to measure overall transmissivity of samples. An optional bandpass filter can be inserted in the optical path between the light source 23 and photodetector to limit colorimetric determinations to a desired wavelength. Additional photodetectors could be included in the probe assembly 20 to allow simultaneous measurements at a plurality of selected wavelengths. Analysis in the near infrared (NIR) region can also be performed by substituting a InGaAs detector in place of a silicon photodetector. The probe can also be used to excite the sample fluid with light at one frequency and detect fluorescence emitted by the sample fluid through a filter at a second frequency.

Another embodiment substitutes a holder suitable for receiving a standard laboratory cuvette in place of the sample chamber 30 shown in the drawings. A series of cuvettes holding samples can be placed in the holder, analyzed, and then removed from the probe 20. This eliminates the need to immerse the probe 20 in larger container of the sample fluid.

The above disclosure sets forth a number of embodiments of the present invention. Other arrangements or embodiments, not precisely set forth, could be practiced under the teachings of the present invention and as set forth in the following claims.

I claim:

1. A spectrophotometric system comprising:
   a probe for at least partial immersion into a sample fluid, said probe having:
   (a) a light source for directing light into at least a portion of said sample fluid; and
   (b) a photodetector for generating a voltage indicative of the intensity of light received by said photodetector; and
   a pH/ISE meter for receiving an input voltage from said probe, applying a predetermined calibration function to said input voltage, and displaying the resulting value.

2. The spectrophotometric system of claim 1 wherein said probe produces a voltage in the range of approximately zero to 1.8 volts.

3. The spectrophotometric system of claim 1 wherein said probe further comprises interface means for receiving said voltage from said photodetector and producing an output voltage for said pH/ISE meter in the range of approximately zero to 1.8 volts.

4. The spectrophotometric system of claim 3 wherein said probe further comprises a housing containing said light source, said photodetector, and said interface means.

5. The spectrophotometric system of claim 3 wherein said probe further comprises a second photodetector generating a reference voltage indicating the intensity of said light source, and wherein said interface means includes means for normalizing said output voltage to compensate for variations in said reference voltage.

6. The spectrophotometric system of claim 1 wherein said probe further comprises a filter between said light source and said photodetector.

7. The spectrophotometric system of claim 1 wherein said probe further comprises a sample chamber providing a predefined optical path from said light source through a portion of said sample fluid to said photodetector.

8. The spectrophotometric system of claim 1 wherein said photodetector measures the absorption of light from said light source by said sample fluid.

9. The spectrophotometric system of claim 1 wherein said photodetector measures the intensity of fluorescence of said sample fluid excited by said light source.

10. A spectrophotometric system comprising:
    a probe having:
    (a) a housing for at least partial immersion into a sample fluid;
    (b) a light source within said housing for directing light into at least a portion of said sample fluid;
    (c) a photodetector within said housing for generating a voltage indicative of the intensity of light received by said photodetector; and
    (d) a sample chamber within said housing providing a predefined optical path from said light source through a portion of said sample fluid to said photodetector; and
    a pH/ISE meter for receiving an input voltage from said probe, applying a predetermined calibration function to said input voltage, and displaying the resulting value.

11. The spectrophotometric system of claim 10 wherein said probe further comprises interface means for receiving said voltage from said photodetector and producing an output voltage for said pH/ISE meter in the range of approximately zero to 1.8 volts.

12. The spectrophotometric system of claim 11 wherein said probe further comprises a second photodetector generating a reference voltage indicating the intensity of said light source, and wherein said interface means includes means for normalizing said output voltage to compensate for variations in said reference voltage.

13. The spectrophotometric system of claim 10 wherein said probe further comprises a filter between said light source and said photodetector.

14. The spectrophotometric system of claim 10 wherein said photodetector measures the absorption of light from said light source by said sample fluid.

15. The spectrophotometric system of claim 10 wherein said photodetector measures the intensity of fluorescence of said sample fluid excited by said light source.

16. A spectrophotometric system comprising:
    a probe for at least partial immersion into a sample fluid, said probe having:
    (a) a light source within said housing for directing light into at least a portion of said sample fluid;
    (b) a photodetector within said housing for generating a voltage indicative of the intensity of light received by said photodetector; and
    (c) interface means within said housing for receiving said voltage from said photodetector and producing a corresponding output voltage within a predetermined range; and
    a pH/ISE meter for receiving said output voltage from said interface means, applying a predetermined calibration function to said voltage, and displaying the resulting value.

17. The spectrophotometric system of claim 16 wherein said output voltage of said interface means is within the range of approximately zero to 1.8 volts.

18. The spectrophotometric system of claim 16 wherein said probe further comprises a housing containing said light source, said photodetector, and said interface means.

19. The spectrophotometric system of claim 16 wherein said probe further comprises a sample chamber providing a predefined optical path from said light source through a portion of said sample fluid to said photodetector.

20. The spectrophotometric system of claim 16 wherein said probe further comprises a second photodetector generating a reference voltage indicating the intensity of said light source, and wherein said interface means includes means for normalizing said output voltage to compensate for variations in said reference voltage.

* * * * *